United States Patent
Goebel et al.

(10) Patent No.: US 10,716,954 B2
(45) Date of Patent: Jul. 21, 2020

(54) TIME OPTIMIZED RADIATION TREATMENT

(71) Applicant: Varian Medical System Particle Therapy GmbH, Troisdorf (DE)

(72) Inventors: Holger Goebel, Numbrecht (DE); Isabel Huth, Kuerten (DE)

(73) Assignee: Varian Medical System Particle Therapy GmbH (DE)

( * ) Notice: Subject to any disclaimer, the term of this patent is extended or adjusted under 35 U.S.C. 154(b) by 0 days.

(21) Appl. No.: 16/091,515

(22) PCT Filed: Apr. 4, 2017

(86) PCT No.: PCT/EP2017/000420
§ 371 (c)(1),
(2) Date: Oct. 4, 2018

(87) PCT Pub. No.: WO2017/174189
PCT Pub. Date: Oct. 12, 2017

(65) Prior Publication Data
US 2019/0126067 A1 May 2, 2019

Related U.S. Application Data

(60) Provisional application No. 62/318,692, filed on Apr. 5, 2016.

(51) Int. Cl.
*A61N 5/10* (2006.01)

(52) U.S. Cl.
CPC .......... *A61N 5/1031* (2013.01); *A61N 5/103* (2013.01); *A61N 5/107* (2013.01); *A61N 5/1037* (2013.01); *A61N 5/1039* (2013.01); *A61N 5/1043* (2013.01); *A61N 5/1049* (2013.01); *A61N 5/1067* (2013.01); *A61N 5/1071* (2013.01);
(Continued)

(58) Field of Classification Search
CPC .... A61N 5/103; A61N 5/1031; A61N 5/1037; A61N 5/1039; A61N 5/1042; A61N 5/1043; A61N 5/1049; A61N 5/1067; A61N 5/107; A61N 5/1071; A61N 5/1077; A61N 2005/1087
See application file for complete search history.

(56) References Cited

U.S. PATENT DOCUMENTS 7,221,733 B1 * 5/2007 Takai .................. A61N 5/1042
378/65
8,467,497 B2 * 6/2013 Lu ........................ A61N 5/1049
378/65
(Continued)

*Primary Examiner* — David E Smith
(74) *Attorney, Agent, or Firm* — Vista IP Law Group, LLP

(57) ABSTRACT

In one embodiment, a method includes receiving treatment information relating to a treatment plan for proton- or ion-beam therapy intended to irradiate a target tissue; receiving machine-limitation information relating to one or more limitations of one or more machines involved in the proton- or ion-beam therapy; determining a time-optimized beam current for a proton or ion beam based on the treatment information and the machine-limitation information, wherein the time-optimized beam current minimizes the time required to deliver a required quantity of monitor units to one of a plurality of spots, wherein each of the plurality of spots is a particular area of the target tissue; and delivering the time-optimized beam current to the particular area.

18 Claims, 9 Drawing Sheets

(52) U.S. Cl.
CPC .... *A61N 5/1077* (2013.01); *A61N 2005/1087* (2013.01)

(56) References Cited

U.S. PATENT DOCUMENTS

| | | | |
|---|---|---|---|
| 2013/0231517 A1* | 9/2013 | Iwamoto | G01T 1/29 600/1 |
| 2014/0005463 A1* | 1/2014 | Jongen | A61N 5/1037 600/1 |
| 2017/0165502 A1* | 6/2017 | Claereboudt | A61N 5/103 |

* cited by examiner

TIME OPTIMIZED RADIATION TREATMENT

PRIORITY

This application claims the benefit, under 35 U.S.C. § 365(c) of International Patent Application No. PCT/EP2017/000420, filed 4 Apr. 2017, which claims the benefit under 35 U.S.C. § 119(e), of U.S. Provisional Patent Application No. 62/318,692, filed 5 Apr. 2016, each of which is incorporated herein by reference.

TECHNICAL FIELD

This disclosure generally relates to radiation treatment.

BACKGROUND

Proton therapy, also called proton beam therapy, is a type of radiation treatment that uses protons rather than X-rays to irradiate diseased tissue. Although this disclosure focuses on describing the invention in terms of a therapy involving a proton beam (i.e., "proton therapy"), it contemplates therapies with other suitable ion beams (i.e., "ion therapy," generally). One advantage of therapy using high energy proton or ion particles is that their path though the tissue stops at a certain depth, depending of the energy of the particle. On their path through the tissue the particles interact with the matter of the tissue and lose energy to the matter of the tissue. Since the particles increasingly lose energy on their path through the tissue, and since the rate of energy loss is higher with decreasing energy of the particles, the particles lose most of their energy at or toward the end of their path through the matter of the tissue, right before they stop. The high energy deposition loss of charged particles at the end of their travel path through the matter of the tissue is called the "Brag Peak." Furthermore, charged particles may be actively steered in a transverse direction (which may be described in x- and y-coordinates) of the particle travel path. By the superposition of charged particles with different energies and by specifying x- and y-positions, one can achieve better three-dimensional dose conformity than with X-ray radiation therapy.

SUMMARY OF PARTICULAR EMBODIMENTS

In particular embodiments, beam currents of a proton or ion beam, or the number of protons or ions per time segment, may be adjusted to minimize the time it takes to irradiate a target area with radiation. Minimizing the treatment time may be beneficial not only for the convenience of the patient and the treating doctor, but also for efficacy and safety, for example in such cases where the patient is required to remain still (e.g., for breath-hold techniques that may be required in destroying tissue within the lungs) or where a target tissue is a moving target. The beam currents may be adjusted according to a treatment plan and one or more limitations to the treatment machine that produces the proton or ion beam and delivers and monitors the radiation dose. The treatment plan may be based on one or more computerized tomography (CT) images, and/or other suitable images derived from a suitable imaging technique, of the target area of the patient's body (e.g., a cancerous tumor), and may include one or more prescriptions for an amount of radiation to deliver to the target area, as well as multiple locations within the target area to deliver the radiation.

Proton or ion therapy combined with a modulated spot-scanning method, or "pencil-beam scanning" method, that spot scans a treatment zone for irradiation carries the benefit of better three-dimensional dose conformity than known therapy methods on the market. With the modulated spot scanning technique, each prescribed x and y position in an isocenter plane may be irradiated individually with respect to prescribed monitor units and energy values. These prescribed values may be listed in a treatment plan (e.g., created by a doctor). The number of spots in a treatment plan may be relatively high in many cases. In order to keep the total irradiation time as short as possible, the algorithm described herein may be employed.

In order to deliver the calculated dose of radiation, the treatment plan may need to be converted to machine parameters, like beam currents of the proton or ion beam, or the number of protons or ions per time segment, magnet currents, and the like. A specialized software may be used to generate the treatment plan. A drawback of existing methods of developing treatment plans is that they cannot predict or take into account durations of exposure (e.g., a duration for each of the spots of a target volume, a duration for each field, a duration for each layer) while developing the treatment plan. The duration, as well as the sequence of the spots, may play an important role in mitigating motion of a target volume during irradiation (e.g., natural organ movement and/or the respiratory or cardiac cycles). An algorithm may be applied which calculates the beam currents of the proton or ion beam, or the number of protons or ions per time segments such so that the patient is treated as fast as possible, taking into consideration all the treatment machines' limitations. In addition the algorithm may determine the duration of each spot of a field, taking into account the time-optimized beam currents of the proton or ion beam, or the time-optimized number of protons or ions per time segments. The determined durations of each spot and of the whole field can be taken into account in developing the treatment plan. An algorithm may be applied to adjust the beam currents of the proton or ion beam, or the number of protons or ions per time segments such that the patient is treated as fast as possible, taking into consideration all the treatment machines' limitations. The algorithm may also specify the beam currents of the proton or ion beam, or the number of protons or ions per time segment, at each spot and at each layer of the target area.

Although this disclosure focuses on using proton beam therapy to irradiate diseased tissue (e.g., to destroy at least a portion thereof), it contemplates irradiating any suitable tissue (e.g., other undesirable tissue) using the methods described herein. The algorithms described herein may be executed using any suitable computing system, or components therein.

DESCRIPTION OF EXAMPLE EMBODIMENTS

Figure 1:
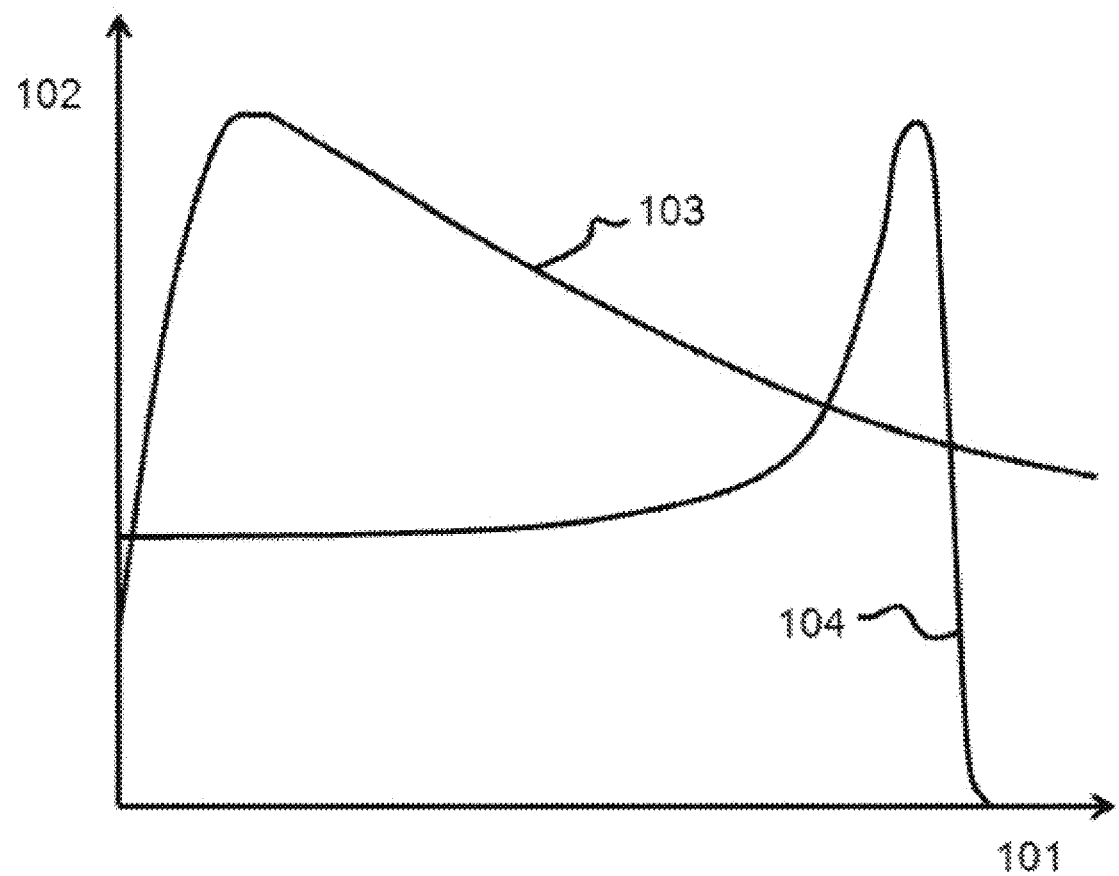
FIG. 1 illustrates example depth-dose distributions for X-rays and protons (or ions).

In particular embodiments, beam currents of the proton or ion beam, or the number of protons or ions per time segment, may be adjusted to minimize the time it takes to treat a target area with radiation. The beam currents of the proton or ion beam, or the number of protons or ions per time segment may be adjusted according to a treatment plan and one or more limitations to the treatment machine equipment that produces the proton or ion beam and delivers and monitors the radiation dose. The treatment plan may be based on one or more CT images, and/or other suitable images derived from a suitable imaging technique, of the target area of the patient's body (e.g., a cancerous tumor), and may include one or more prescriptions for an amount of radiation to deliver to the target area, as well as multiple locations within the target area to deliver the radiation.

In order to deliver the prescribed dose of radiation, the treatment plan may be converted to machine parameters (e.g., beam currents of the proton or ion beam or the number of protons or ions per time segment to be emitted by the accelerator, magnet currents, settings to achieve the prescribed energy of protons or ions at the target volume, measurement range of dose monitor system, etc.). This conversion may take into account the limitations of the treatment machines' equipment that produce the proton or ion beam and deliver and monitor the radiation treatment. For example, a particular treatment machine may have an upper limit for the beam currents of the proton or ion beam, or an upper limit for the number of protons or ions per time segment (e.g., as may limited by the devices of the accelerator, the energy selection system, and/or the beam transfer line). As another example, the equipment of the dose monitoring system may have upper and lower limits for the beam current of the proton or ion beam, or may have upper and lower limits of the number of protons or ions per time segments (e.g., it may be out of the measurement range). As another example, the equipment of the beam position and beam shape monitoring system may have upper and lower limits for the beam current of the proton or ion beam, or may have upper and lower limits of the number of protons or ions per time segments (e.g., it may be out of the measurement ranges). In particular embodiments, an algorithm may be applied to adjust the beam currents of the proton or ion beam, or the number of protons or ions per time segments so that the treatment time is as short as possible, taking into consideration all the machines' limitations and the minimum amount of time needed to complete the irradiation of a spot or layer. For example, the beam current may be set as high as possible for either each layer or each spot, in order to minimize the treatment time and to accommodate the treatment machine limitations. In particular embodiments, the algorithm may specify the beam currents of the proton or ion beam, or the number of protons or ions per time segments for each spot and/or for each layer of the target area. For example, the algorithm may specify beam currents of the proton or ion beam, or the number of protons or ions per time segments for each layer, where all spots in the same layer are irradiated with the same beam current of the proton or ion beam, or with same the number of protons or ions per time segments. As another example, the algorithm may specify the beam currents of the proton or ion beam, or the number of protons or ions per time segments for each spot, where all spots in the field may be irradiated with different beam currents.

A specialized software may be used to generate the treatment plan. A drawback of existing methods of developing treatment plans is that they cannot predict or take into account durations of exposure (e.g., a duration for each of the spots of a target volume, a duration for each field, a duration for each layer) while developing the treatment plan. The duration, as well as the sequence of the spots, may play an important role in mitigating motion of a target volume during irradiation (e.g., natural organ movement and/or the respiratory or cardiac cycles). An algorithm may be applied which calculates the beam currents of the proton or ion beam, or the number of protons or ions per time segments such so that the patient is treated as fast as possible, taking into consideration all the treatment machines' limitations. In addition the algorithm may determine the duration of each spot of a field, taking into account the time-optimized beam currents of the proton or ion beam, or the time-optimized number of protons or ions per time segments. The determined durations of each spot and of the whole field can be taken into account in developing the treatment plan.

FIG. 1 illustrates example depth-dose distributions for X-rays and protons (or ions). Proton or ion therapy may be superior to x-ray radiation therapy in terms of its ability to prevent damage to surrounding healthy tissue. X-axis 101 shows the depth of the particles and y-axis 102 shows the proportional radiation dose delivered at a given depth. The proportional dose of radiation delivered by the photons in x-ray radiation therapy is shown by photon dose distribution line 103. Photon dose distribution line 103 peaks at a low depth and then gradually tapers out. To increase the radiation delivered at a desired depth, damage to the healthy tissue above the tumor may be proportionally increased. In comparison, proton (or ion) dose distribution line 104 minimizes the radiation delivered before and after the target and delivers nearly all of its energy in a given window of depth. The peak of the proton or ion dose distribution line is called the Bragg peak.

Protons or ions may be accelerated to suitable energy using a particle accelerator. Some common types of particle accelerators are cyclotrons (e.g., normal- or super-conducting cyclotrons), synchrotrons (e.g., normal- or super-conducting synchrotrons), and synchrocyclotrons (e.g., normal- or super-conducting synchrocyclotrons). These accelerators may depend on the interplay of magnetic and electric fields. Synchrotrons may accelerate particles through a path having a constant radius and adjust the magnetic and electric fields as the particles gain momentum. Cyclotrons may accelerate charged particles using a high-frequency alternating voltage. A perpendicular magnetic field may cause the particles to move in an expanding spiral wherein they re-encounter the accelerating voltage. When the particles reach a predetermined radius they may be guided out of the cyclotron in an accelerated state.

When a patient comes in for cancer treatment, a CT scan may be performed, and/or other suitable imaging technique, to determine the size, shape, and location of a diseased tissue. Images from the CT scan (or other suitable technique) may produce a three-dimensional image of diseased tissue in the patient's body. Using the images, a treatment plan for that patient is produced. A specialized software to aid with the development of the treatment plan may be used. The treatment plan may define, among other things, (1) the treatment volume or a target volume; (2) the radiation dose; (3) location to deposit radiation; and (4) field and fraction parameters. In particular embodiments, the specialized software may include a means for rendering a virtual visualization of time dependent application during the treatment planning process (prior to treatment). The software may allow the doctors to evaluate treatment efficacy of one or more potential treatment plans. For example, it may render a simulated overlay of target movement (e.g., caused by the patient's breathing or other action), and may also simulate the effects of applying different doses to different areas at different times.

"Treatment volume" refers to the entire volume that will be subject to radiation—this may include both the "target volume" (e.g., the volume that defines a diseased tissue) and the surrounding healthy tissue and organs. With proton or ion beam therapy, radiation delivered to surrounding healthy tissue and organs may be minimized, so treatment volume and target volume may be roughly equivalent.

The radiation dose may be measured in gray units. One gray is defined as the absorption of one joule of radiation energy per one kilogram of matter. Based on the defined target tissue (e.g., a diseased tissue) and the prescribed radiation dose the specialized software to aid with the development of the treatment plan determines the energy per spot, the number of monitor units (or in some cases the number of protons or ions) per spot, and the beam position in x- and y-coordinates in an isocenter plane per spot. Additional parameters (e.g. incident angle of the beam, position of the patient, etc.) are determined using the specialized software to aid with the development of the treatment plan.

A treatment plan may contain the parameters for each field. A field is the direction from which the target volume gets irradiated, i.e. the direction from which the beam is shot or the incident angle, and the patient position with respect to the incident angle. A patient may receive radiation with one or multiple fields. For example, if a proton beam is delivered to the body from directly above the body (e.g., 0 degrees), that may be a first field. At a second time, a second proton beam may be delivered from 30 degrees, and this may be a second field. At a third time, a third proton beam may be delivered from 60 degrees, and this may be a third field.

Most treatments of diseased tissue with a prescribed total dose are split into several "fractions". Each fraction will irradiate a "fraction" of the total prescribed dose. For example, a prescribed total dose may be broken up over 20 to 30 "fractions" that may occur over the course of several weeks.

An example treatment plan may include a target volume that defines a volume of the diseased tissue that is to be targeted by the proton- or ion-beam therapy; a set of spots that specify a prescribed beam position in x- and y-coordinates per spot at an isocenter, wherein the x- and y-coordinates are transversal to a beam direction, a prescribed energy of the proton or ion beam per spot, and a prescribed amount of monitor units per spot; a set of field parameters that specify a direction from which the proton or ion beam is to be shot, a position of the target volume, and treatment specific parameters for one or more fields; and a fraction parameter that specifies a portion of the radiation dose that is to be delivered for a given radiation session.

In order to deliver the prescribed dose of radiation, the proper beam currents of the proton or ion beam, or the number of protons or ions per time segment are calculated for each fraction of radiation dose, an algorithm may calculate the beam currents of the proton or ion beam, or the number of protons or ions per time segment for each energy layer. This means that all spots on the same energy layer may be irradiated with the same the beam currents of the proton or ion beam (or the same the number of protons or ions per time segment). The algorithm may also take into account the treatment machine parameters and limitations. The beam current of the proton or ion beam (or the number of protons or ions per time segment for a given energy layer) may be calculated by taking the ratio of "monitor units" (e.g., how many protons are necessary to effectively treat a location on the tumor) to the "minimum spot duration" (e.g., the minimum time to stay at a spot before moving to the next spot). The algorithm may check whether this ratio is larger than the upper limit of the dose monitor system or the beam position and beam shape monitor system. If so, the beam current, or the number of protons or ions per time segment, may be set to the upper limit. The algorithm may also check whether any of the calculated beam currents, or the calculated number of protons or ions per time segment, is higher than the upper limit of the accelerator. If so, the beam current, or the number of protons or ions per time segment, may be set to the upper limit.

Figure 2:
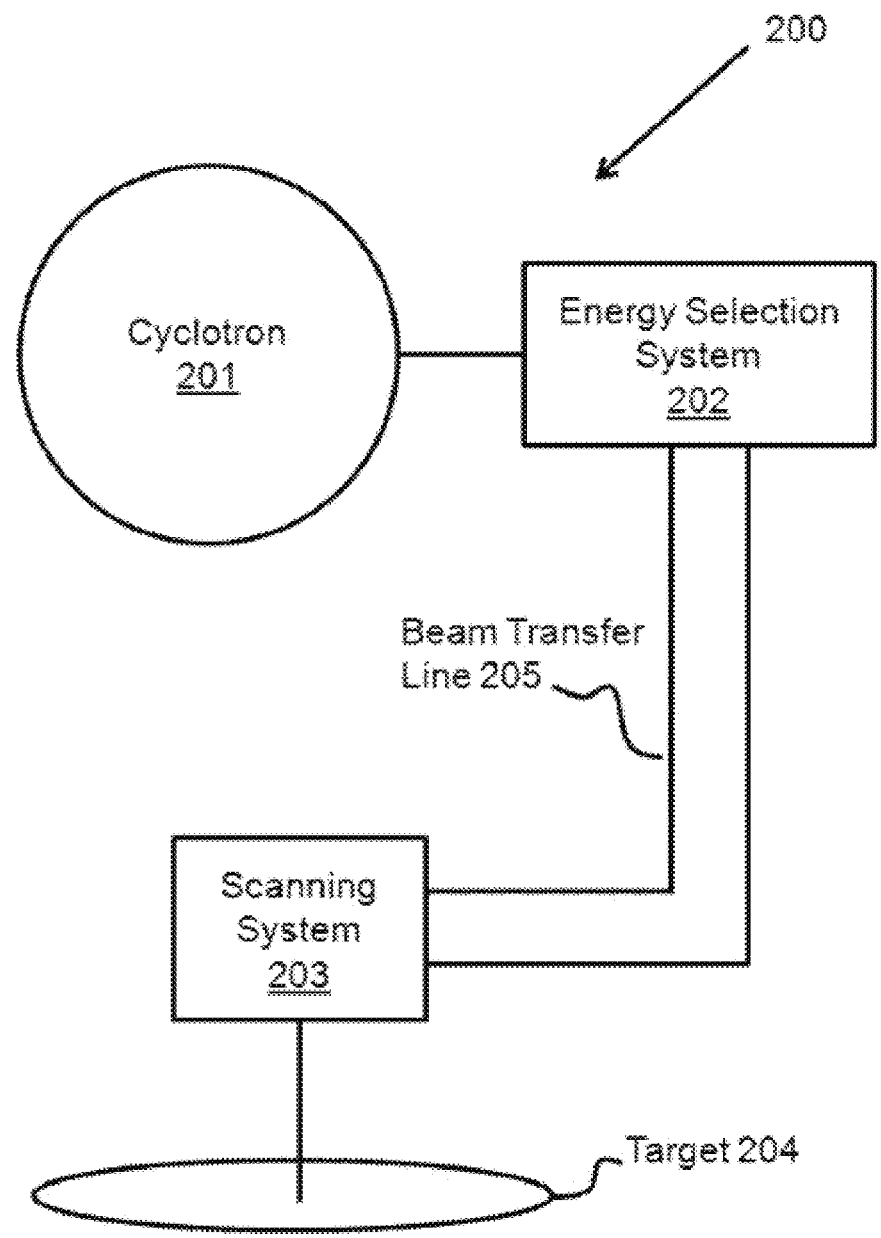
FIG. 2 illustrates an example apparatus of the treatment machine for irradiating a target in a time-optimized manner.

FIG. 2 illustrates an example apparatus for irradiating a target in a time-optimized manner. System 200 comprises cyclotron 201, which is configured to generate a proton beam. In particular embodiments, cyclotron 201 may be a superconducting cyclotron. The energy level for protons in the proton beam may be selected using energy selection system 202. Energy selection system 202 may be capable of setting an energy level continuously up to the fixed energy of the accelerated protons by the cyclotron. In particular embodiments, this energy selection may be based on a first information which may be deterministic information provided by the treatment plan or provided by a system that derives this information. Scanning system 203 may guide the proton beam to a location on target 204 using a magnet system. In particular embodiments, scanning system 203 may guide the proton beam according to a second information which may be deterministic information provided by the treatment plan or provided by a system that derives this information. In particular embodiments, system 200 may be capable of three-dimensional spot scanning or pencil beam scanning. In these embodiments, the energy of the protons in the proton beam may be set to the prescribed values in the treatment plan for each spot, and to the prescribed transversal coordinates of the beam for each spot by adjusting the magnet system of the scanning system. Adjusting the energy of the beam may allow control of the depth at which the Bragg Peaks of the accelerated protons are located. The increased flexibility made available through three-dimensional spot scanning may greatly improve the precision of the dose delivered to a patient so as to maximize dose delivery to a tumor and minimize damage to healthy tissue.

Spot scanning of target 204 can be conducted in accordance with several variant methodologies. In particular embodiments, target 204 may be a tumor and the location to which the proton beam is guided may be selected based on patient location data regarding a specific patient who is undergoing proton radiation therapy. The patient location data may include information about the location of certain anatomical structures within a patient and may also include the location of a tumor within the patient's body. Spot scanning of target 204 (e.g., a portion of diseased tissue) may be conducted in multiple sessions, "fractions", with the same or variant spot scanning patterns. In particular embodiments, scanning system 203 and energy selection system 202 may both alter their values during a given application of protons so that three-dimensional spot scanning may be achieved. In particular embodiments, the beam current of the proton beam or the number of protons per time segment may be altered along with the energy of the proton beam and/or with the transversal coordinates to more accurately control the delivery of radiation to the target at a specific location. In particular embodiments, scanning system 203 may adjust the location of beam delivery during an application while the energy level remains constant so that the protons may be applied in a transversally varying manner while the depth of the Bragg Peak may remain constant or nearly constant. In order to have a medically significant effect on tumors, a single session of proton radiation therapy may not need to be great in duration. For example, the irradiation of a single field of a fraction may take several seconds or even less than one second.

System 200 may additionally comprise a beam transfer line 205. In particular embodiments, beam transfer line 205 may have multiple junctions having magnets or other devices for guiding the beam through various paths. In particular embodiments, certain paths may be shut-off while others remain open. Beam transfer line 205 may lead the proton beam from Energy Selection System 202 to Scanning System 203, or the Scanning System may be in between the devices of the beam transfer line. In particular embodiments, target 204 may be a diseased tissue in a patient's body or some other target for proton beam irradiation.

Figure 3:
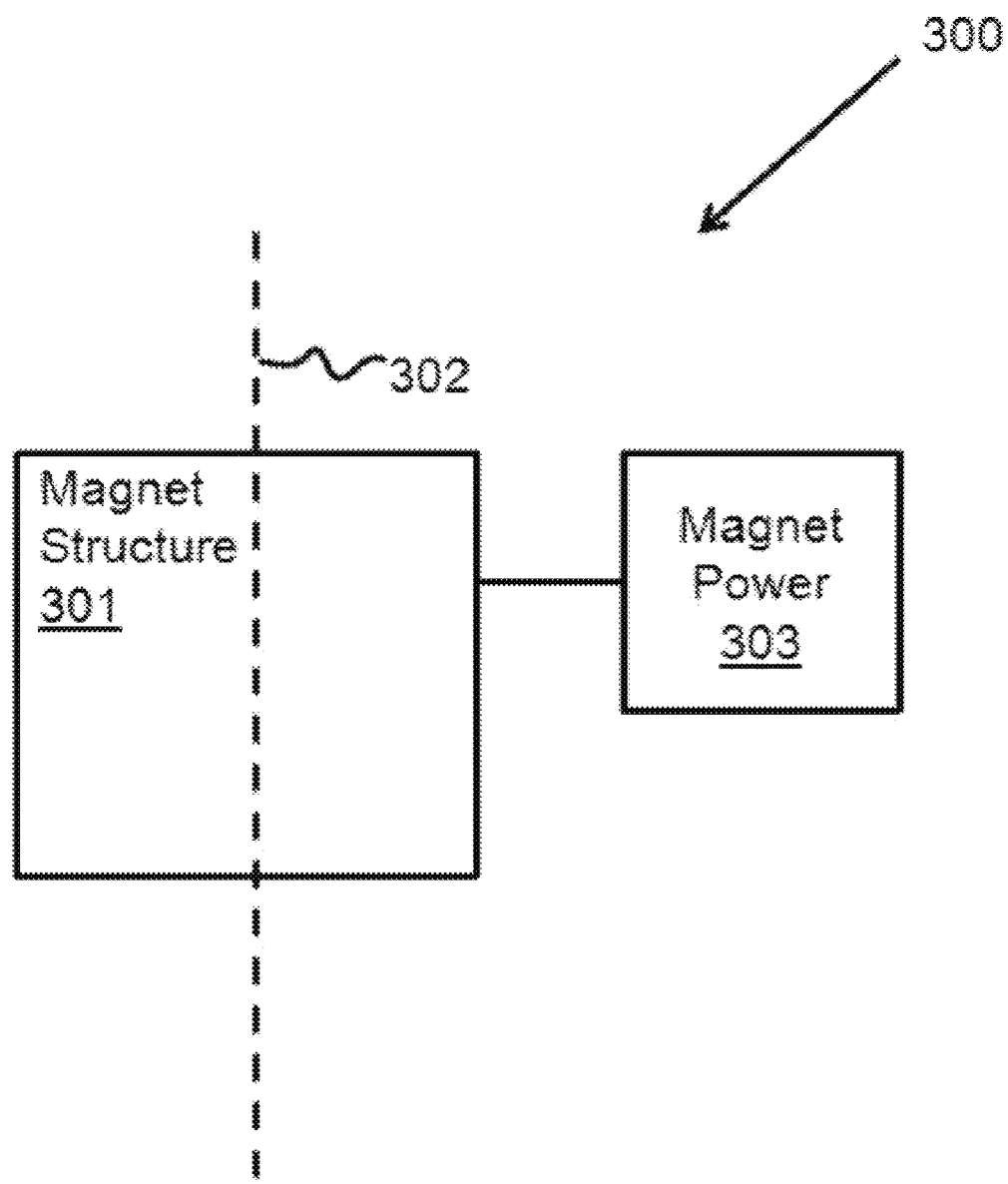
FIG. 3 illustrates an example magnet system of the treatment machine in the accelerator, energy selection system, beam transfer line, or scanning system for irradiating a target in a time-optimized manner.

FIG. 3 illustrates an example magnet system 300 comprising a magnet structure 310 and magnet power supply 303. A magnet system may be part of the accelerator, energy selection system, beam transfer line, and the scanning system. Referencing FIG. 3 and FIG. 4, scanning system 400 may comprise a magnet system 300 used to guide proton beam 302. Magnet structure 301 may be caused to alter its magnetic field to guide the magnet in transversal x- and y-directions. In particular embodiments, power may be provided to magnet structure 301 through magnet power supply 303. In particular embodiments, magnet power supply 303 may be controlled based on the energy of the proton beam and the target beam position, x- and y-directions, at the target.

Figure 4:
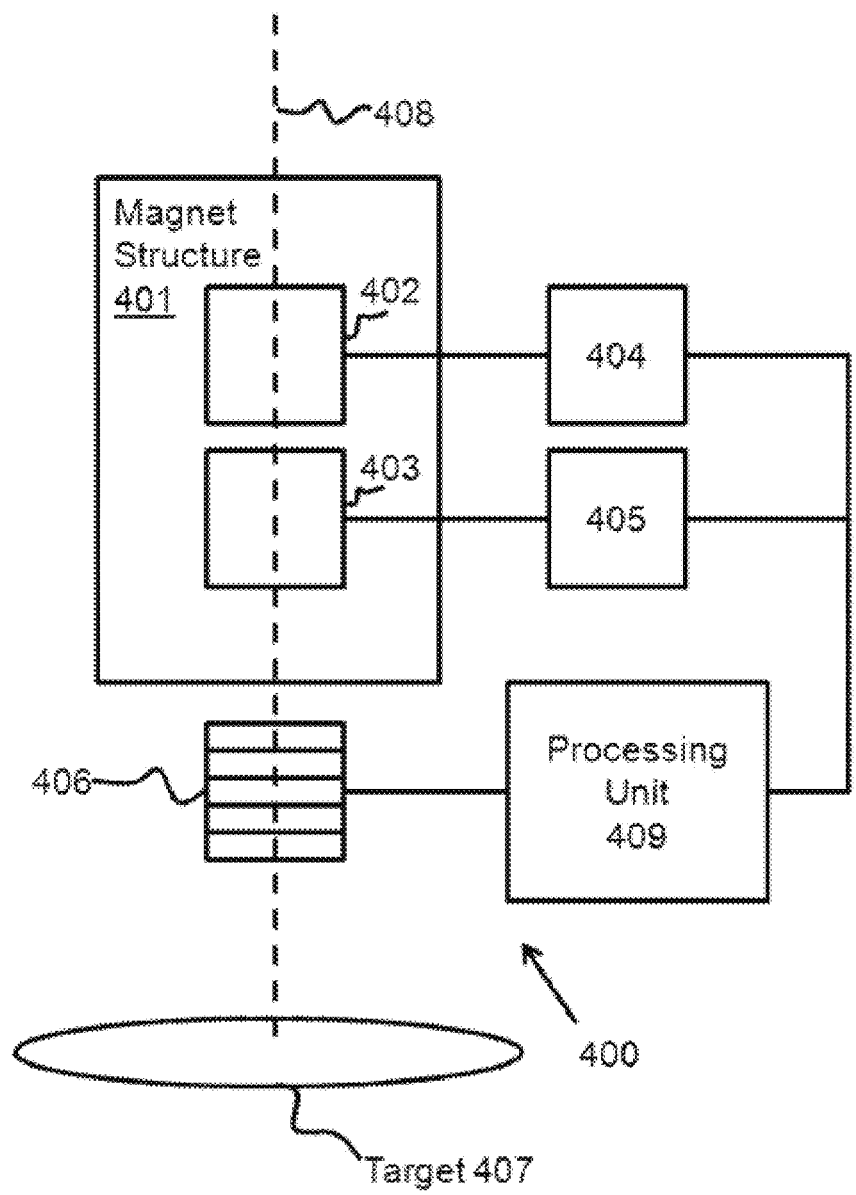
FIG. 4 illustrates an example scanning system of the treatment machine for irradiating a target in a time-optimized manner.

FIG. 4 illustrates an example scanning system for irradiating a target in a time-optimized manner. Scanning system 400 may comprises a magnet structure 401 used to guide the proton beam. In particular embodiments, magnet structure 401 may comprise two scanning magnets as shown by y-directional magnet 402 and x-directional magnet 403. In particular embodiments, the magnets may be powered by separate power supplies as shown by first magnet power supply 404 and second magnet power supply 405. Y-directional magnet may be capable of steering the proton beam in a transversal y-direction. X-directional magnet 403 may be capable of steering the proton beam in a transversal x-direction. In particular embodiments, a magnet structure may comprise one scanning magnet, which may be a bi-directional magnet. In particular embodiments, the bi-directional magnet may include two pairs of coils—one for the x-direction and one for the y-direction. In particular embodiments, the coils of the bi-directional magnet are powered by separate power supplies. The bi-directional magnet may be capable of steering the proton beam in a transversal y-direction and a transversal x-direction, as necessary.

In particular embodiments, the scanning system may additionally comprise a transition ionization chamber such as transition ionization chamber 406. This transition ionization chamber may be interspersed between magnet structure 401 and target 407 along proton beam path 408. Transition ionization chamber 406 may be configured to measure the dose delivered to target 407, i.e., it may work as the dose monitor system. In particular embodiments, the dose delivered may be tracked for a particular location on target 407. In particular embodiments, the dose delivered may be tracked for the entire target 407. In particular embodiments, transition ionization chamber 406 may be a multi-strip ionization chamber comprising several millimeter-wide strips of conductive foil connected to electronic sensors. Multi-strip ionization chamber 406 may be configured to measure an actual beam position and beam shape on target 407 relative to the targeted location.

In particular embodiments, the data collected by transition ionization chamber 406 can be applied for various uses. As shown in FIG. 4, the collected data could be sent to real-time processing unit 409. In particular embodiments, real-time processing unit 409 may use information regarding the beam position, dose or monitor units, treatment duration, and patient location data such as the depth of the tumor to direct magnet structure 401 so as to optimize the irradiation of target 407. For example, real-time processing unit 409 may determine that the beam position does not match the desired location and may compensate for this deviation (e.g., by adjusting the beam position) to more accurately match the beam position with the desired location. As another example, real-time processing unit 409 may take in patient-specific data in real-time regarding the position of the tumor and adjust the location to which the proton beam is directed, and/or adjust the energy of the proton beam to affect penetration depth. In particular embodiments, real-time processing unit 409 may deliver a first information item to energy selection system 202. For example, this first information item may be the depth of the tumor in a patient undergoing proton radiation therapy or the proton beam energy. In particular embodiments, real-time processing unit 409 may deliver a second information item to other components in scanning system 400. For example, this second information item may be the beam position and target dose or data derived from beam position and target dose. In these examples, the system may make adjustments based on the first information, the second information, and/or other suitable real-time information. Real-time processing unit 409 therefore may allow for real-time adjustment of the beam position, beam currents or number of protons or ions per time segment, and Bragg peak depth based on patient specific information and actual measurement the proton beam's characteristics and location. In particular embodiments, the adjustment may be performed automatically within the treatment machine, in response to an external device, or in response to an input by an operator of the system. In particular embodiments, the data collected by transition ionization chamber 406 could be output from the system for external use. In particular embodiments, the real-time information may include a real-time virtual visualization of the proton beam therapy.

Figure 5:
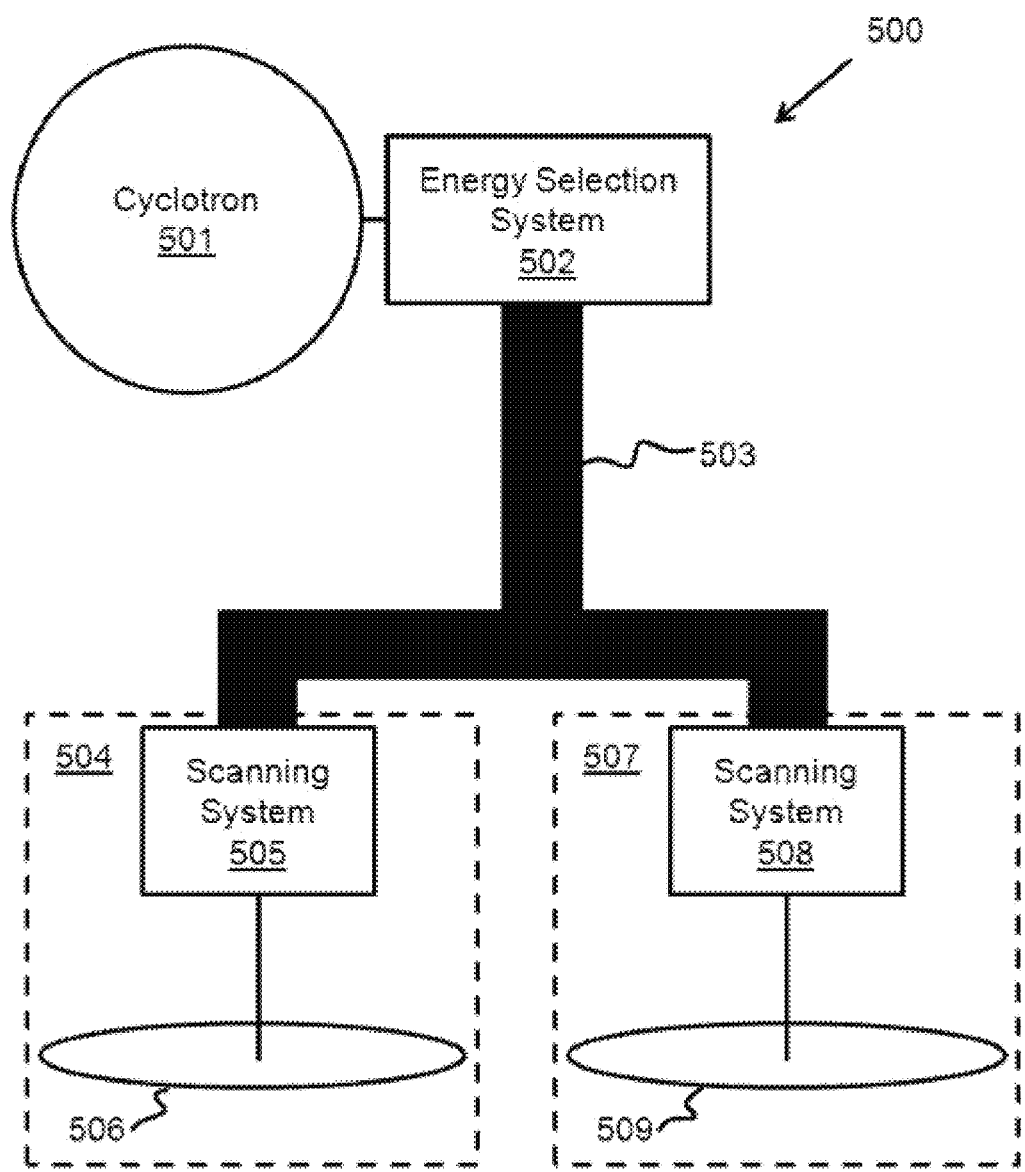
FIG. 5 illustrates an example of the treatment machine for routing a proton beam to multiple treatment locations.

FIG. 5 illustrates an example system for routing proton beams to multiple locations. FIG. 5 illustrates system 500. System 500 may comprise a cyclotron 501 and an energy selection system 502. System 500 may additionally comprise a beam transfer line 503. In particular embodiments, beam transfer line 503 may have multiple junctions having magnet systems or other devices for guiding the beam through various paths. In particular embodiments, certain beam paths may be shut off while others remain open. Beam transfer line 503 may guide the beam to patient treatment room 504, which may have first scanning system 505 and first target 506. In particular embodiments, target 506 may be a tumor in a patient's body or some other target for proton beam irradiation. Beam transfer line 503 may also guide the beam to second patient treatment room 507 which may have second scanning system 508 and second target 509. In particular embodiments, scanning system 505 or scanning system 508 may have characteristics in accordance with those of scanning system 203. The treatment machines comprising the two systems may have treatment machine limitations that are same or different. In a case where the two systems have different treatment machine limitations, the disclosed algorithm may calculate different optimized beam currents or number of protons or ions per time segment and irradiation times (e.g., setting the beam current or number of protons or ions per time segment of each system to the upper limits of their respective treatment machines). Although FIG. 5 only illustrates a system for routing proton beams to two scanning systems, this disclosure contemplates a system for routing proton beams to any suitable number of scanning systems.

In particular embodiments, energy selection system 502 may have characteristics in accordance with those of energy selection system 202. In particular embodiments, energy selection system 502 may be able to receive patient specific information and proton beam related information from processing units in scanning system 505 and scanning system 508 as well as from other scanning systems to which beam transfer line 503 is connected. In particular embodiments, patient treatment room 504 and patient treatment room 507 may be separate locations in the same facility. In other embodiments, they may be separate locations in different facilities that still utilize the same cyclotron 501. Using a single cyclotron in this manner may allow for the cost-effective utilization of the cyclotron.

Figure 6:
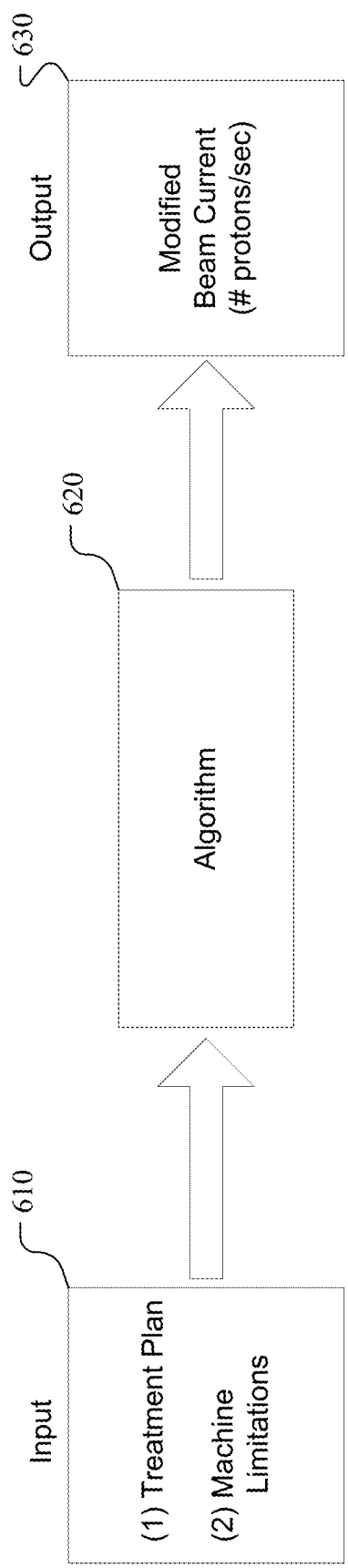
FIG. 6 illustrates an example block diagram of the inputs and outputs for an algorithm used for irradiating a target in a time-optimized manner.

FIG. 6 illustrates an example block diagram of the inputs and outputs for an algorithm used for irradiating a target in a time-optimized manner. Input parameters 610 may include the treatment plan and the limitations of the particular treatment machines (e.g., treatment machine parameters) that are being used to produce the proton or ion beam and to deliver and monitor the radiation treatment. Such treatment machines may include any or all of the treatment machines discussed herein, or any other treatment machine that is used in radiation treatment. The treatment plan may include the target volume, the treatment volume, one or more locations on the tumor to deliver radiation (e.g., specified by a set of energy per spot, monitor units or number of proton or number of ions per spot, x-y coordinates at an isocenter for each spot), field and fraction parameters, a recommended beam current (e.g., the beam current to be used without accounting for machine limitations), and the time of exposure. These factors are explained herein.

The machine parameters may include any combination of the following parameters: minimum spot duration (e.g., the minimum time to apply a beam current to a spot before moving on to the next spot); beam current or the number of protons or ions per time segment at isocenter; beam current or the number of protons or ions per time segment from the accelerator; monitoring limits or tolerances for the monitor unit; monitoring limits for the scanning magnet currents; and monitoring limits or tolerances for the beam position and beam shape. The signals of the dose monitor system, beam position monitor system, and beam shape monitor system may have upper and lower limits. For example, there may be upper and lower limits on the beam current or the number of protons or ions per time segment (e.g. measurement range). These limits may depend on the beam energy at isocenter, and the dose and position monitors parameters themselves); and the beam current of the treatment machine (e.g., the treatment machine may have an upper limit for a beam current; this may depend on the beam energy).

From the defined target volume and the prescribed radiation dose the specialized software to aid with the development of the treatment plan determines the energy per spot, the number of monitor units per spot, and the beam position in x and y in the isocenter plane per spot. Instead of monitor units per spot (see IEC 60601 technical standards), "Scan Spot Meterset Weights" per spot (see NEMA DICOM RT standard), or in some cases the number of protons or ions per spot are given by the treatment plan. Spot scanning may deliver a planned irradiation with a given spot monitor unit, position, and energy. Algorithm 620 may minimize the irradiation time for which the monitor units at each spot is applied. This may occur in at least two different ways: (1) apply radiation to each single spot in the treatment plan with the beam current being adjusted for each energy layer individually; or (2) apply radiation to each single spot in the treatment plan, with the beam current being adjusted for each single spot. The first way may irradiate each energy layer as fast as possible; the second way may irradiate each spot as fast as possible.

Algorithm 620 may calculate the beam current (number of protons per second) or rate of monitor units for each spot separately and taking into account the treatment machine parameters. The "beam current" or "rate of monitor units" may be calculated for each spot by the ratio of "monitor units" (e.g., prescribed by the treatment plan) to "minimum spot duration" (e.g., the minimum amount of time to stay at a spot before moving to the next spot). This "beam current" or "rate of monitor units" may need to be checked if the value of the ratio is larger than the upper limit of dose monitor system and the beam position and beam shape monitor system. If this is the case the "beam current" or "rate of monitor units" may be set to the upper limit. In addition, it may be necessary to check if this "beam current" or "rate of monitor units" is higher than the upper limit of the treatment machine (e.g., a proton or ion accelerator). If this is the case the "beam current" or "rate of monitor units" may be set to the upper limit. Similarly, if this new "beam current" or "rate of monitor units" is lower than a lower limit (e.g., a minimum beam current) of the dose monitor system and the beam position and beam shape monitor system or of the irradiation machine, an error message may be displayed to the user, with the information of the problem. This error case may not occur when all devices of the treatment machine are designed, installed and commissioned correctly. Alternatively or additionally, the beam current may be set to the lower limit. The algorithm may also check for beam current or number of proton or ion per time segment limitations on the energy selection system and the beam transfer line, which refers to the trajectory of the proton beam. For example, it may check for limitations with respect to measuring the beam with the dose monitor system and the beam position and beam shape monitor system or generating the beam with the treatment machine.

Algorithm 620 may calculate the beam current (number of protons per second) or rate of monitor units for each energy layer separately (e.g., all spots with the same energy may be irradiated with the same "beam current" or "rate of monitor units" and taking into account the treatment machine parameters). The "beam current" or "rate of monitor units" for a set of spots within the same energy layer may be calculated by the ratio of "monitor units" to "minimum spot duration." In particular embodiments, the smallest spot monitor unit value in a set of spot monitor values corresponding to the set of spots may be used. This "beam current" or "rate of monitor units" may need to be checked if the value of the ratio is larger than the upper limit of the dose monitor system, the beam position, and/or the beam shape monitor system. If this is the case the "beam current" or "rate of monitor units" may be set to the upper limit. In addition, it may be necessary to check if this "beam current" or "rate of monitor units" is higher than the upper limit of the treatment machine (e.g., a proton or ion accelerator). If this is the case the "beam current" or "rate of monitor units" may be set to the upper limit. If this new "beam current" or "rate of monitor units" is lower than a lower limit (e.g., a minimum beam current) of the dose monitor system and the beam position and beam shape monitor system or of the irradiation machine, an error message may be displayed to the user, with the information of the problem. It needs to be noted, that this error case may not occur when all devices of the treatment machine are designed, installed, and commissioned correctly. The algorithm may also check for beam current or number of proton or ion per time segment limitations on the energy selection system and the beam transfer line, which refers to the trajectory of the proton beam. For example, it may check for limitations with respect to measuring the beam with the dose monitor system and the beam position and beam shape monitor system or generating the beam with the treatment machine.

The two inputs (e.g., the treatment plan and treatment machine limitations) may be fed into algorithm 620, and the algorithm may process the inputs and produce an adjusted beam current or adjusted number of protons per time segment for the accelerator, and the beam current at dose monitor system and the beam position and beam shape monitor system as output parameter 630. This adjusted beam current may take into consideration the treatment plan and the machine limitations, and may allow for radiation treatment to be completed with a minimum amount of time.

Figure 7:
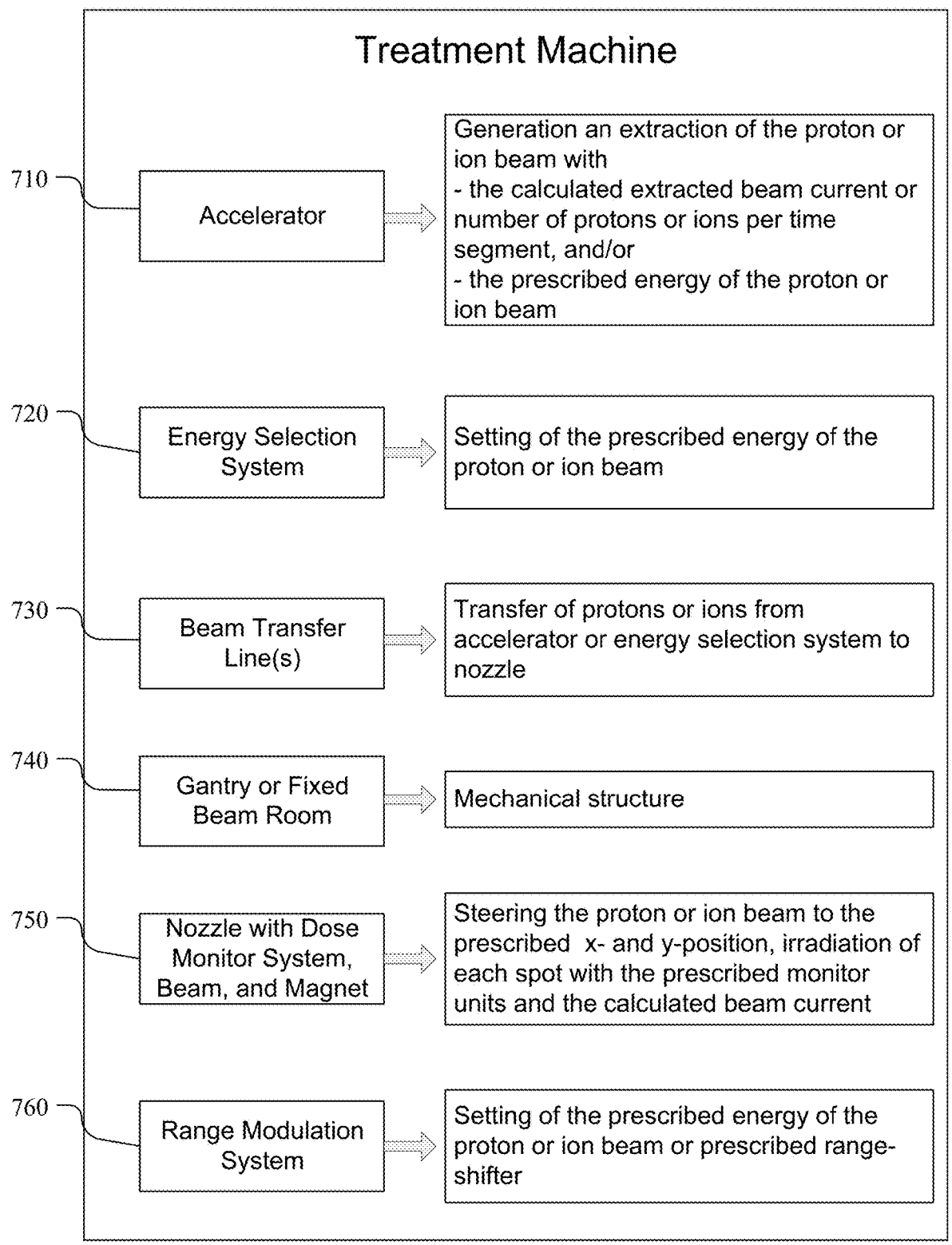
FIG. 7 illustrates an example block diagram of system components of the described treatment system and their example functionalities.

FIG. 7 illustrates an example block diagram of system components of the described treatment system 700 and their example functionalities. In particular embodiments, the energy of the proton (or ion) beam may set by an accelerator 710 of the treatment machine itself, an energy selection system 720, and/or a range modulation system 760 (e.g., at or near the location of the patient). In particular embodiments, the energy selection system 720 may modify the energy of the proton (or ion) beam delivery from the accelerator. In particular embodiments, in order to guide the beam from the accelerator 710 to the nozzle 750, the treatment system may be equipped optionally with a beam transfer line 730. The beam transfer line 730 may have multiple junctions having magnets and/or other devices for guiding the proton or ion beam through various paths to one or more nozzles. In particular embodiments, the energy selection system 720 of the treatment system 700 may consist of devices used together with the beam transfer line 730.

In particular embodiments, the range modulation system 760 may modify the beam energy of the proton (or ion) beam at the nozzle 750 (which may be upstream or downstream the primary and secondary dose monitor system (e.g., IEC 60601-2-64)), right before the beam hits a treatment area of the patient, and/or at any other suitable location.

In particular embodiments, the nozzle may comprise a magnet structure which may have the capability to steer the proton (or ion) beam in a transversal y-direction and transversal x-direction. In addition, in particular embodiments, the nozzle may comprise the primary and secondary dose monitor systems (e.g., IEC 60601-2-64), and a beam position and beam shape monitor system. The components of the treatment system may be either fully or partly installed at position 740 (which may be a gantry or a fixed beam room). The gantry may be a mechanical structure that facilitates the performing of the irradiation of the treatment volume from different directions. A fixed beam room may be a room that facilitates the performing of the irradiation of the treatment volume from one direction.

In particular embodiments, using the modulated spot scanning technique, the treatment system 700 may irradiate each prescribed x and y position in an isocenter plane individually with the prescribed monitor units, and with respect to the prescribed energy of the proton (or ion) beam. The prescribed energy of the proton or ion beam may be set in any suitable manner (e.g., as described herein). The prescribed values may be listed in a treatment plan (e.g., one that is specific to the patient or a group of patients). In particular embodiments, the treatment system 700 may adjust the beam current for each spot, or each energy layer respectively, as may have been calculated.

Figure 8:
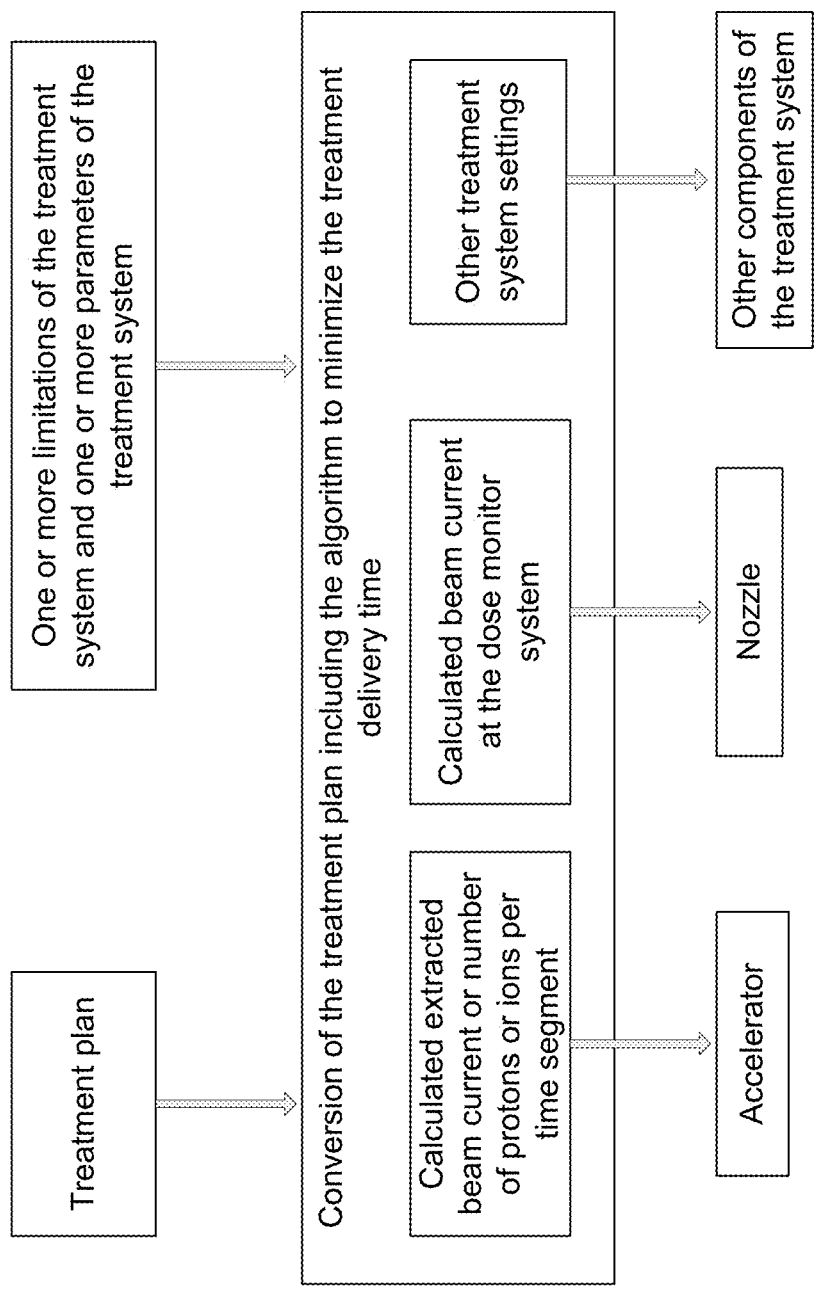
FIG. 8 illustrates an example block diagram of the handling of inputs and the specific outputs for an algorithm used for irradiating a target in a time-optimized manner.

FIG. 8 illustrates an example block diagram of the handling of inputs and the specific outputs for an algorithm used for irradiating a target in a time-optimized manner. Similar to FIG. 6, FIG. 8 provides only a high-level description of an example embodiment.

In particular embodiments, when the beam current "$I_{beam}$" is set for each layer or energy E, the beam current at the dose monitor system for each layer may be calculated as follows. For each layer "layer_number," the beam current "$I_{beam}$ (layer_number)" may be calculated by the fraction of the smallest monitor unit value "$MU_{min}$" and the minimum spot duration "$T_{min}$," and may be multiplied optionally with a factor "F", which describes the energy losses of the proton or ion beam in the dose monitor system or any other dose monitor system specific correction. An example of a generalized, high level layer algorithm is described below:

Part 1 of example layer algorithm:

$$I_{beam}(\text{layer\_number}) = MU_{min}(\text{layer\_number})/T_{min}*F$$

In the next steps the treatment system limitations may be taken into account. As an example, the measurement range of the dose monitor system and the beam position and beam shape monitor system, "I_min_monitors" and "I_max_monitors", are considered:

Part 2 of example layer algorithm:

```
If I_beam(layer_number) > I_max_monitors then
    I_beam(layer_number) = I_max_monitors
Endif
If I_beam(layer_number) < I_min_monitors then
    Error_with_identifier
Endif
```

As a further example, the maximum or minimum beam current at the dose monitor system limited by the devices of the accelerator, the energy selection system, and/or beam transfer line are considered, "I_min" and "I_max." For example, I_min may be the minimum possible extracted beam current of the accelerator times the so-called transmission of the energy selection system and beam transfer line, and I_max may be the maximum possible extracted beam current of the accelerator times the so-called transmission of the energy selection system and beam transfer line.

Part 3 of example layer algorithm:

```
If I_beam(layer_number) > I_max then
    I_beam(layer_number) = I_max
    If I_beam(layer_number) < I_min_monitors then
        Error_with_identifier
    Endif
Endif
If I_beam(layer_number) < I_min then
    Error_with_identifier
Endif
```

In the example algorithm directly above, the error messages should not occur if the machine configuration of the treatment planning system, the treatment system, and the measurement range of the treatment system dose monitor system are designed correctly. Although the example algorithm considers particular example system limitations, any other suitable limitations can be taken into account by plugging them into any suitable combination of Parts 2 and 3 of the example algorithm.

In the next step, the algorithm calculates either the beam current (or number of protons or ions per second) from the accelerator, $I_{accelerator}$, or the number of extracted protons or ions per time segment from the accelerator, $N_{accelerator}$. In the equations below, "S" is the ratio between the beam current at the dose monitor system $I_{beam}$ and the beam current from the accelerator $I_{accelerator}$, and "time_segment" is the duration of one or more time segments during which the accelerator extracts protons or ions. S may depend on the energy, the Gantry angle, and/or the beam spot size.

Part 4 of example layer algorithm:

```
I_accelerator(layer_number) = I_beam(layer_number) / S   or
N_accelerator(layer_number) = I_beam(layer_number) / S * time_segment
```

Part 5 of example layer algorithm:

$$T(\text{spot\_number}) = MU(\text{spot\_number})/I_{beam}(\text{layer\_number}) * F$$

The ratio "S" depends of the implementation of the treatment machine. For example, it can depend on the beam energy of the layer, one or more treatment machine limitations, and/or one or more treatment machine parameters. T(spot_number) is the duration of each spot during the irradiation.

In particular embodiments, when the beam current "$I_{beam}$" is set for each spot, the beam current at the dose monitor system for each spot is calculated as follows. For each spot "spot_number", the beam current "$I_{beam}$(spot_number)" may be calculated by of the fraction of the prescribed monitor unit value "MU" and the minimum spot duration "$T_{min}$", and may be multiplied optionally with a factor "F", which describes the energy losses of the proton or ion beam in the dose monitor system or any other dose monitor system specific correction. An example of a generalized, high level spot algorithm is described below:

Part 1 of example spot algorithm:

$$I_{beam}(\text{spot\_number}) = MU(\text{spot\_number})/T_{min} * F$$

In the next steps the treatment system limitations are taken into account. As an example, the measurement range of the dose monitor system and the beam position and beam shape monitor system, "I_min_monitors" and "I_max_monitors", are considered.

Part 2 of example spot algorithm:

```
If I_beam(spot_number) > I_max_monitors then
    I_beam(spot_number) = I_max_monitors
Endif
If I_beam(spot_number) < I_min_monitors then
    Error_with_identifier
Endif
```

As a further example, the maximum or minimum beam current at the dose monitor system limited by the devices of the accelerator, and/or the energy selection system, and/or beam transfer line are considered, "I_min" and "I_max." For example, I_min may be the minimum possible extracted beam current of the accelerator times the so-called transmission of the energy selection system and beam transfer line, and I_max may be the maximum possible extracted beam current of the accelerator times the so-called transmission of the energy selection system and beam transfer line.

Part 3 of example spot algorithm:

```
If I_beam(spot_number) > I_max then
    I_beam(spot_number) = I_max
    If I_beam(spot_number) < I_min_monitors then
        Error_with_identifier
    Endif
Endif
If I_beam(spot_number) < I_min then
    Error_with_identifier
Endif
```

In the example algorithm directly above, the error messages should not occur if the machine configuration of the treatment planning system, the treatment system, and the measurement range of the treatment system dose monitor system are designed correctly. Although the example algorithm considers particular example system limitations, any other suitable limitations can be taken into account by plugging them into any suitable combination of Parts 2 and 3 of the example algorithm.

In the next step, the algorithm may calculate either the beam current (or number of protons or ions per second) from the accelerator, $I_{accelerator}$, or the number of extracted protons or ions per time segment from the accelerator, $N_{accelerator}$. In the equations below, "S" is the ratio between the beam current at the dose monitor system $I_{beam}$ and the beam current from the accelerator $I_{accelerator}$, and "time_segment" is the duration of one or more time segments during which the accelerator extracts protons or ions. S may depend on the energy, the Gantry angle, and/or the beam spot size.

Part 4 of spot algorithm:

```
I_accelerator(spot_number) = I_beam(spot_number) / S   or
N_accelerator(spot_number) = I_beam(spot_number) / S * time_segment
```

Part 5 of example spot algorithm:

$$T(\text{spot\_number}) = MU(\text{spot\_number})/I_{beam}(\text{layer\_number}) * F$$

The ratio "S" depends of the implementation of the treatment machine, for example it can depend on the beam energy of the layer, one or more treatment machine limitations and/or one or more treatment machine parameters. T(spot_number) may be the duration of each spot during the irradiation.

In particular embodiments, in the example algorithms (layer and spot algorithms) describe above, the minimum spot duration "$T_{min}$" may have a value of any suitable range. For example, it may be in the range of milliseconds. More generally, it may for example, range from 1 µs to several seconds, depending on the design of the treatment system.

All determined machine parameter from the treatment plan including the beam current or number of protons (or ions) per second from the accelerator may be calculated by the algorithm, described herein.

Figure 9:
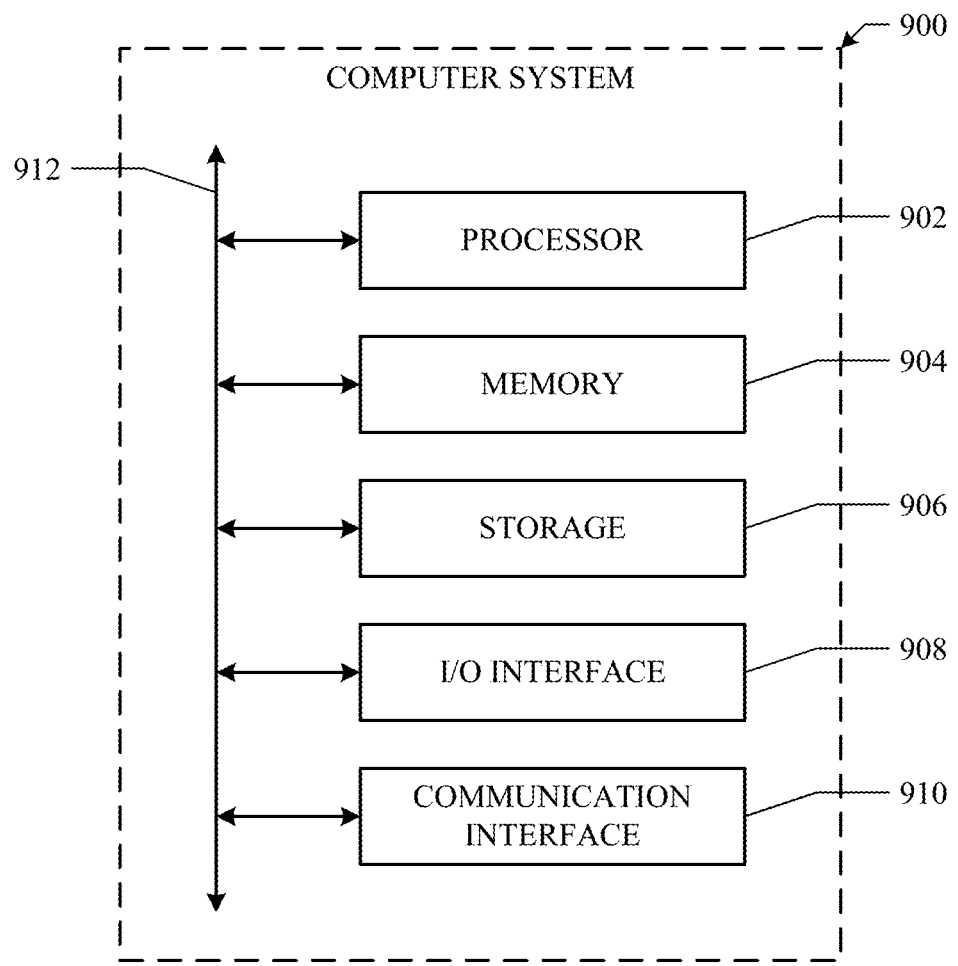
FIG. 9 illustrates an example computer system.

FIG. 9 illustrates an example computer system 900 that may be used to execute the instructions involved in the algorithm used for irradiating a target in a time-optimized manner. In particular embodiments, one or more computer systems 900 may perform one or more steps of one or more methods described or illustrated herein. In particular embodiments, one or more computer systems 900 may provide functionality described or illustrated herein. In particular embodiments, software running on one or more computer systems 900 may perform one or more steps of one or more methods described or illustrated herein or provide functionality described or illustrated herein. Particular embodiments may include one or more portions of one or more computer systems 900. Herein, reference to a computer system may encompass a computing device, and vice versa, where appropriate. Moreover, reference to a computer system may encompass one or more computer systems, where appropriate.

This disclosure contemplates any suitable number of computer systems 900. This disclosure contemplates computer system 900 taking any suitable physical form. As example and not by way of limitation, computer system 900 may be an embedded computer system, a system-on-chip (SOC), a single-board computer system (SBC) (such as, for example, a computer-on-module (COM) or system-on-module (SOM)), a desktop computer system, a laptop or notebook computer system, an interactive kiosk, a mainframe, a mesh of computer systems, a mobile telephone, a personal digital assistant (PDA), a server, a tablet computer system, an augmented/virtual reality device, or a combination of two or more of these. Where appropriate, computer system 900 may include one or more computer systems 900; be unitary or distributed; span multiple locations; span multiple machines; span multiple data centers; or reside in a cloud, which may include one or more cloud components in one or more networks. Where appropriate, one or more computer systems 900 may perform without substantial spatial or temporal limitation one or more steps of one or more methods described or illustrated herein. As an example and not by way of limitation, one or more computer systems 900 may perform in real-time or in batch mode one or more steps of one or more methods described or illustrated herein. One or more computer systems 900 may perform at different times or at different locations one or more steps of one or more methods described or illustrated herein, where appropriate.

In particular embodiments, computer system 900 may include a processor 902, memory 904, storage 906, an input/output (I/O) interface 908, a communication interface 910, and a bus 912. Although this disclosure describes and illustrates a particular computer system having a particular number of particular components in a particular arrangement, this disclosure contemplates any suitable computer system having any suitable number of any suitable components in any suitable arrangement.

In particular embodiments, processor 902 may include hardware for executing instructions, such as those making up a computer program. As an example and not by way of limitation, to execute instructions, processor 902 may retrieve (or fetch) the instructions from an internal register, an internal cache, memory 904, or storage 906; decode and execute them; and then write one or more results to an internal register, an internal cache, memory 904, or storage 906. In particular embodiments, processor 902 may include one or more internal caches for data, instructions, or addresses. This disclosure contemplates processor 902 including any suitable number of any suitable internal caches, where appropriate. As an example and not by way of limitation, processor 902 may include one or more instruction caches, one or more data caches, and one or more translation lookaside buffers (TLBs). Instructions in the instruction caches may be copies of instructions in memory 904 or storage 906, and the instruction caches may speed up retrieval of those instructions by processor 902. Data in the data caches may be copies of data in memory 904 or storage 906 for instructions executing at processor 902 to operate on; the results of previous instructions executed at processor 902 for access by subsequent instructions executing at processor 902 or for writing to memory 904 or storage 906; or other suitable data. The data caches may speed up read or write operations by processor 902. The TLBs may speed up virtual-address translation for processor 902. In particular embodiments, processor 902 may include one or more internal registers for data, instructions, or addresses. This disclosure contemplates processor 902 including any suitable number of any suitable internal registers, where appropriate. Where appropriate, processor 902 may include one or more arithmetic logic units (ALUs); be a multi-core processor; or include one or more processors 902. Although this disclosure describes and illustrates a particular processor, this disclosure contemplates any suitable processor.

In particular embodiments, memory 904 may include main memory for storing instructions for processor 902 to execute or data for processor 902 to operate on. As an example and not by way of limitation, computer system 900 may load instructions from storage 906 or another source (such as, for example, another computer system 900) to memory 904. Processor 902 may then load the instructions from memory 904 to an internal register or internal cache. To execute the instructions, processor 902 may retrieve the instructions from the internal register or internal cache and decode them. During or after execution of the instructions, processor 902 may write one or more results (which may be intermediate or final results) to the internal register or internal cache. Processor 902 may then write one or more of those results to memory 904. In particular embodiments, processor 902 executes only instructions in one or more internal registers or internal caches or in memory 904 (as opposed to storage 906 or elsewhere) and operates only on data in one or more internal registers or internal caches or in memory 904 (as opposed to storage 906 or elsewhere). One or more memory buses (which may each include an address bus and a data bus) may couple processor 902 to memory 904. Bus 912 may include one or more memory buses, as described below. In particular embodiments, one or more memory management units (MMUs) reside between processor 902 and memory 904 and facilitate accesses to memory 904 requested by processor 902. In particular embodiments, memory 904 includes random access memory (RAM). This RAM may be volatile memory, where appropriate. Where appropriate, this RAM may be dynamic RAM (DRAM) or static RAM (SRAM). Moreover, where appropriate, this RAM may be single-ported or multi-ported RAM. This disclosure contemplates any suitable RAM. Memory 904 may include one or more memories 904, where appropriate. Although this disclosure describes and illustrates particular memory, this disclosure contemplates any suitable memory.

In particular embodiments, storage 906 may include mass storage for data or instructions. As an example and not by way of limitation, storage 906 may include a hard disk drive (HDD), a floppy disk drive, flash memory, an optical disc, a magneto-optical disc, magnetic tape, or a Universal Serial Bus (USB) drive or a combination of two or more of these. Storage 906 may include removable or non-removable (or fixed) media, where appropriate. Storage 906 may be internal or external to computer system 900, where appropriate. In particular embodiments, storage 906 is non-volatile, solid-state memory. In particular embodiments, storage 906 includes read-only memory (ROM). Where appropriate, this ROM may be mask-programmed ROM, programmable ROM (PROM), erasable PROM (EPROM), electrically erasable PROM (EEPROM), electrically alterable ROM (EAROM), or flash memory or a combination of two or more of these. This disclosure contemplates mass storage 906 taking any suitable physical form. Storage 906 may include one or more storage control units facilitating communication between processor 902 and storage 906, where appropriate. Where appropriate, storage 906 may include one or more storages 906. Although this disclosure describes and illustrates particular storage, this disclosure contemplates any suitable storage.

In particular embodiments, I/O interface 908 may include hardware, software, or both, providing one or more interfaces for communication between computer system 900 and one or more I/O devices. Computer system 900 may include one or more of these I/O devices, where appropriate. One or more of these I/O devices may enable communication between a person and computer system 900. As an example and not by way of limitation, an I/O device may include a keyboard, keypad, microphone, monitor, mouse, printer, scanner, speaker, still camera, stylus, tablet, touch screen, trackball, video camera, another suitable I/O device or a combination of two or more of these. An I/O device may include one or more sensors. This disclosure contemplates any suitable I/O devices and any suitable I/O interfaces 908 for them. Where appropriate, I/O interface 908 may include one or more device or software drivers enabling processor 902 to drive one or more of these I/O devices. I/O interface 908 may include one or more I/O interfaces 908, where appropriate. Although this disclosure describes and illustrates a particular I/O interface, this disclosure contemplates any suitable I/O interface.

In particular embodiments, communication interface 910 may include hardware, software, or both providing one or more interfaces for communication (such as, for example, packet-based communication) between computer system 900 and one or more other computer systems 900 or one or more networks. As an example and not by way of limitation, communication interface 910 may include a network interface controller (NIC) or network adapter for communicating with an Ethernet or other wire-based network or a wireless NIC (WNIC) or wireless adapter for communicating with a wireless network, such as a WI-FI network. This disclosure contemplates any suitable network and any suitable communication interface 910 for it. As an example and not by way of limitation, computer system 900 may communicate with an ad hoc network, a personal area network (PAN), a local area network (LAN), a wide area network (WAN), a metropolitan area network (MAN), or one or more portions of the Internet or a combination of two or more of these. One or more portions of one or more of these networks may be wired or wireless. As an example, computer system 900 may communicate with a wireless PAN (WPAN) (such as, for example, a BLUETOOTH WPAN), a WI-FI network, a WI-MAX network, a cellular telephone network (such as, for example, a Global System for Mobile Communications (GSM) network), or other suitable wireless network or a combination of two or more of these. Computer system 900 may include any suitable communication interface 910 for any of these networks, where appropriate. Communication interface 910 may include one or more communication interfaces 910, where appropriate. Although this disclosure describes and illustrates a particular communication interface, this disclosure contemplates any suitable communication interface.

In particular embodiments, bus 912 may include hardware, software, or both coupling components of computer system 900 to each other. As an example and not by way of limitation, bus 912 may include an Accelerated Graphics Port (AGP) or other graphics bus, an Enhanced Industry Standard Architecture (EISA) bus, a front-side bus (FSB), a HYPERTRANSPORT (HT) interconnect, an Industry Standard Architecture (ISA) bus, an INFINIBAND interconnect, a low-pin-count (LPC) bus, a memory bus, a Micro Channel Architecture (MCA) bus, a Peripheral Component Interconnect (PCI) bus, a PCI-Express (PCIe) bus, a serial advanced technology attachment (SATA) bus, a Video Electronics Standards Association local (VLB) bus, or another suitable bus or a combination of two or more of these. Bus 912 may include one or more buses 912, where appropriate. Although this disclosure describes and illustrates a particular bus, this disclosure contemplates any suitable bus or interconnect.

Herein, a computer-readable non-transitory storage medium or media may include one or more semiconductor-based or other integrated circuits (ICs) (such, as for example, field-programmable gate arrays (FPGAs) or application-specific ICs (ASICs)), hard disk drives (HDDs), hybrid hard drives (HHDs), optical discs, optical disc drives (ODDs), magneto-optical discs, magneto-optical drives, floppy diskettes, floppy disk drives (FDDs), magnetic tapes, solid-state drives (SSDs), RAM-drives, SECURE DIGITAL cards or drives, any other suitable computer-readable non-transitory storage media, or any suitable combination of two or more of these, where appropriate. A computer-readable non-transitory storage medium may be volatile, non-volatile, or a combination of volatile and non-volatile, where appropriate.

Herein, "or" is inclusive and not exclusive, unless expressly indicated otherwise or indicated otherwise by context. Therefore, herein, "A or B" means "A, B, or both," unless expressly indicated otherwise or indicated otherwise by context. Moreover, "and" is both joint and several, unless expressly indicated otherwise or indicated otherwise by context. Therefore, herein, "A and B" means "A and B, jointly or severally," unless expressly indicated otherwise or indicated otherwise by context.

The scope of this disclosure encompasses all changes, substitutions, variations, alterations, and modifications to the example embodiments described or illustrated herein that a person having ordinary skill in the art would comprehend. The scope of this disclosure is not limited to the example embodiments described or illustrated herein. Moreover, although this disclosure describes and illustrates respective embodiments herein as including particular components, elements, feature, functions, operations, or steps, any of these embodiments may include any combination or permutation of any of the components, elements, features, functions, operations, or steps described or illustrated anywhere herein that a person having ordinary skill in the art would comprehend. Furthermore, reference in the appended claims to an apparatus or system or a component of an apparatus or system being adapted to, arranged to, capable of, configured to, enabled to, operable to, or operative to perform a particular function encompasses that apparatus, system, component, whether or not it or that particular function is activated, turned on, or unlocked, as long as that apparatus, system, or component is so adapted, arranged, capable, configured, enabled, operable, or operative. Additionally, although this disclosure describes or illustrates particular embodiments as providing particular advantages, particular embodiments may provide none, some, or all of these advantages.

What is claimed is:

1. A method comprising, by one or more devices:
   receiving treatment information relating to a treatment plan for proton- or ion-beam therapy intended to irradiate a target tissue;
   receiving machine-limitation information relating to one or more limitations of one or more machines involved in the proton- or ion-beam therapy, wherein the machine-limitation information comprises information related to an upper limit of:
     a dose-monitor system involved in the proton or ion beam therapy, wherein the upper limit of the dose-monitor system is a maximum beam current that the dose-monitor system is capable of monitoring, or
     a beam-position and beam-shape monitoring system involved in the proton or ion beam therapy, wherein the upper limit is a maximum beam current that the beam-position and beam-shape monitoring system is capable of monitoring;
   determining a time-optimized beam current for a proton or ion beam based on the treatment information and the machine-limitation information, wherein the time-optimized beam current minimizes the time required to deliver a required quantity of monitor units to one of a plurality of spots, wherein each of the plurality of spots is a particular area of the target tissue; and
   delivering the proton or ion beam based on the time-optimized beam current to the particular area.

2. The method of claim 1, wherein the treatment plan specifies:
   a target volume that defines a volume of the target tissue;
   a set of spots that specify a prescribed beam position in x- and y-coordinates per spot at an isocenter, wherein the x- and y-coordinates are transversal to a beam direction, a prescribed energy of the proton or ion beam per spot, and a prescribed amount of monitor units per spot;
   a set of field parameters that specify a direction from which the proton or ion beam is to be shot, a position of the target volume, and treatment specific parameters for one or more fields; and
   a fraction parameter that specifies a portion of the radiation dose that is to be delivered for a given radiation session.

3. The method of claim 1, wherein the machine-limitation information comprises information related to a maximum beam current.

4. The method of claim 1, wherein the determining of the time-optimized beam current comprises, for each energy layer of a target volume with respect to a particular field:
   determining a smallest value of prescribed monitor units for the each energy layer from all prescribed spots in the each energy layer;
   determining a minimum time of exposure required to deliver the prescribed monitor units;
   calculating a ratio of the smallest value of prescribed monitor units per energy layer to the determined minimum time of exposure; and
   if the calculated ratio is higher than the maximum beam current specified by the machine-limitation information for the dose-monitor system or the beam-position and beam-shape monitoring system involved in the proton- or ion-beam therapy,
     setting the time-optimized beam current for the each energy layer to the maximum beam current for the dose-monitor system or the beam-position and beam shape-monitoring system.

5. The method of claim 4, further comprising:
   if the calculated ratio is higher than the maximum beam current specified by the machine-limitation information for an accelerator involved in the proton- or ion-beam therapy,
     setting the time-optimized beam current for each energy layer to the maximum beam current for the accelerator.

6. The method of claim 4, further comprising:
   determining a spot duration for each spot based on the time-optimized beam current for each energy layer.

7. The method of claim 4, further comprising:
   determining a spot duration for each spot based on a time-optimized beam current determined for each spot.

8. The method of claim 1, wherein the determining of the time-optimized beam current comprises:
   determining a minimum time of exposure required to deliver the determined radiation dose;
   calculating a ratio of a prescribed amount of monitor units to the determined minimum time of exposure for each spot of a field; and
   if the calculated ratio is higher than the maximum beam current specified by the machine-limitation information for the dose-monitor system or the beam-position and beam shape-monitoring system,
     setting the time-optimized beam current for each of the plurality of spots to the maximum beam current for the dose-monitor system or the beam-position and beam shape-monitoring system.

9. The method of claim 8, further comprising:
   if the calculated ratio is higher than the maximum beam current specified by the machine-limitation information for an accelerator involved in the proton- or ion-beam therapy,
     setting the time-optimized beam current for each of the plurality of spots to the maximum beam current for the accelerator.

10. The method of claim 1, wherein each of the plurality of spots is defined by one or more x-locations and one or more y-locations of a target volume prescribed in the treatment plan.

11. The method of claim 1, wherein the particular area is an energy layer on the target tissue, wherein the energy layer is defined by one or more z-locations of a target volume prescribed in the treatment plan.

12. The method of claim 1, further comprising:
   monitoring a real-time beam position and beam shape of the proton or ion beam and a real-time amount of monitor units delivered to the particular area; and adjusting the position of the proton beam, an intensity of the beam, and a depth of the proton beam based on the real-time position, the real-time radiation dose, and the real-time location.

13. The method of claim 1, wherein the target tissue is diseased tissue.

14. The method of claim 1, wherein the proton or ion beam is generated using a cyclotron or a synchrotron.

15. A system comprising:
one or more processors; and
one or more computer-readable non-transitory storage media coupled to one or more of the processors and comprising instructions operable when executed by one or more of the processors to cause the system to:
receive treatment information relating to a treatment plan for proton- or ion-beam therapy intended to irradiate a target tissue;
receive machine-limitation information relating to one or more limitations of one or more machines involved in the proton- or ion-beam therapy, wherein the machine-limitation information comprises information related to an upper limit of:
a dose-monitor system involved in the proton or ion beam therapy, wherein the upper limit of the dose-monitor system is a maximum beam current that the dose-monitor system is capable of monitoring, or
a beam-position and beam-shape monitoring system involved in the proton or ion beam therapy, wherein the upper limit is a maximum beam current that the beam-position and beam-shape monitoring system is capable of monitoring;
determine a time-optimized beam current for a proton or ion beam based on the treatment information and the machine-limitation information, wherein the time-optimized beam current minimizes the time required to deliver a required quantity of monitor units to one of a plurality of spots, wherein each of the plurality of spots is a particular area of the target tissue; and
deliver the proton or ion beam based on the time-optimized beam current to the particular area.

16. The system of claim 15, wherein the determining of the time-optimized beam current comprises, for each energy layer of a target volume with respect to a particular field:
determining a smallest value of prescribed monitor units for the each energy layer from all prescribed spots in the each energy layer;
determining a minimum time of exposure required to deliver the prescribed monitor units;
calculating a ratio of the smallest value of prescribed monitor units per energy layer to the determined minimum time of exposure; and
if the calculated ratio is higher than the maximum beam current specified by the machine-limitation information for the dose-monitor system or the beam-position and beam-shape monitoring system involved in the proton- or ion-beam therapy,
setting the time-optimized beam current for the each energy layer to the maximum beam current for the dose-monitor system or the beam-position and beam shape-monitoring system.

17. The system of claim 16, wherein the instructions are further operable when executed by one or more of the processors to cause the system to:
if the calculated ratio is higher than the maximum beam current specified by the machine-limitation information for an accelerator involved in the proton- or ion-beam therapy,
set the time-optimized beam current for each energy layer to the maximum beam current for the accelerator.

18. One or more computer-readable non-transitory storage media comprising software that is operable when executed to:
receive treatment information relating to a treatment plan for proton- or ion-beam therapy intended to irradiate a target tissue;
receive machine-limitation information relating to one or more limitations of one or more machines involved in the proton- or ion-beam therapy, wherein the machine-limitation information comprises information related to an upper limit of:
a dose-monitor system involved in the proton or ion beam therapy, wherein the upper limit of the dose-monitor system is a maximum beam current that the dose-monitor system is capable of monitoring, or
a beam-position and beam-shape monitoring system involved in the proton or ion beam therapy, wherein the upper limit is a maximum beam current that the beam-position and beam-shape monitoring system is capable of monitoring;
determine a time-optimized beam current for a proton or ion beam based on the treatment information and the machine-limitation information, wherein the time-optimized beam current minimizes the time required to deliver a required quantity of monitor units to one of a plurality of spots, wherein each of the plurality of spots is a particular area of the target tissue; and
deliver the proton or ion beam based on the time-optimized beam current to the particular area.

* * * * *